(12) United States Patent
Serizawa et al.

(10) Patent No.: US 11,505,813 B2
(45) Date of Patent: Nov. 22, 2022

(54) CELLOOLIGOSACCHARIDE PRODUCTION METHOD

(71) Applicants: DAI-ICHI KOGYO SEIYAKU CO., LTD., Kyoto (JP); TOKYO INSTITUTE OF TECHNOLOGY, Tokyo (JP)

(72) Inventors: Takeshi Serizawa, Tokyo (JP); Toshiki Sawada, Tokyo (JP); Masahito Nishiura, Kyotoshi (JP)

(73) Assignees: DAI-ICHI KOGYO SEIYAKU CO., LTD., Kyoto (JP); TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 17/052,017

(22) PCT Filed: Apr. 11, 2019

(86) PCT No.: PCT/JP2019/015839
§ 371 (c)(1),
(2) Date: Oct. 30, 2020

(87) PCT Pub. No.: WO2019/211971
PCT Pub. Date: Nov. 7, 2019

(65) Prior Publication Data
US 2021/0238641 A1 Aug. 5, 2021

(30) Foreign Application Priority Data
May 2, 2018 (JP) .............................. JP2018-088774

(51) Int. Cl.
*C12P 19/18* (2006.01)
*C12P 19/04* (2006.01)

(52) U.S. Cl.
CPC .............. *C12P 19/18* (2013.01); *C12P 19/04* (2013.01); *C12Y 204/01049* (2013.01)

(58) Field of Classification Search
CPC ... C12P 19/18; C12P 19/04; C12Y 204/01049
See application file for complete search history.

(56) References Cited

U.S. PATENT DOCUMENTS

2020/0390798 A1* 12/2020 Gibson ................ A61K 31/736

FOREIGN PATENT DOCUMENTS

JP 2001-112496 A 4/2001

OTHER PUBLICATIONS

K.D. Winter et al. "Chemoenzymatic Synthesis of β-D-Glucosides using Cellobiose Phosphorylase from Clostridium thermocellum", Advanced Synthesis and Catalysis 357:1961-1969 (Year: 2015).*
K.D. Winter et al. "Ionic liquids as cosolvents for glycosylation by sucrose phosphorylase: balancing acceptor solubility and enzyme stability", Green Chemistry 15:1949-1955 (Year: 2013).*
Adharis et al., Environmentally friendly pathways towards the synthesis of vinyl-based oligocelluloses. Carbohydrate Polymers, 2018, vol. 193: 196-204, available online Mar. 30, 2018. (Year: 2018).*
Arai et al., Purification and Properties of Cellodextrin Phosphorylase from Clostridium thermocellum . J. Ferment. Bioengineering., 1994, vol. 77(3): 239-242. (Year: 1994).*
Hata et al., Enzyme-Catalyzed Bottom-Up Synthesis of Mechanically and Physicochemically Stable Cellulose Hydrogels for Spatial Immobilization of Functional Colloidal Particles. Biomacromolecules, 2018, vol. 19: 1269-1275, published Mar. 19, 2018. (Year: 2018).*
Hiraishi et al., "Synthesis of highly ordered cellulose II in vitro using cellodextrin phosphorylase", Carbohydrate Research, 2009, vol. 344, pp. 2468-2473.
International Search Report (PCT/ISA/210) issued in PCT/JP2019/015839 dated Jul. 9, 2019.
Written Opinion (PCT/ISA/237) issued in PCT/JP2019/015839 dated Jul. 9, 2019.

* cited by examiner

*Primary Examiner* — Ganapathirama Raghu
(74) *Attorney, Agent, or Firm* — Birch, Stewart, Kolasch & Birch, LLP

(57) ABSTRACT

A method for producing a cellooligosaccharide that enables the formation of a cellooligosaccharide having a high degree of polymerization to be suppressed in enzymatic synthesis of a cellooligosaccharide, the method comprising reacting α-glucose-1-phosphate and at least one primer selected from the group consisting of glucose, cellobiose, and alkylated glucose with cellodextrin phosphorylase in a mixed solvent containing water and a water-soluble organic solvent.

6 Claims, 4 Drawing Sheets

CELLOOLIGOSACCHARIDE PRODUCTION METHOD

TECHNICAL FIELD

The present invention relates to a method for producing a cellooligosaccharide using an enzyme.

BACKGROUND ART

A known method for producing a cellulose oligomer, i.e., a cellooligosaccharide, using an enzyme is a synthesis method using the reverse reaction of cellodextrin phosphorylase, a phosphorolytic enzyme.

For example, Non-patent Literature 1 discloses that cellooligosaccharides with an average degree of polymerization of 9 are synthesized by reacting α-glucose-1-phosphate and glucose as a primer with cellodextrin phosphorylase.

Patent Literature 1 discloses that cellooligosaccharides with a degree of polymerization of 2 to 6 are synthesized by allowing α-glucan phosphorylase to act on soluble starch to produce glucose-1-phosphate, and reacting the obtained glucose-1-phosphate with cellobiose phosphorylase and cellodextrin phosphorylase in the presence of glucose.

CITATION LIST

Patent Literature

PTL 1: JP2001-112496A

Non-Patent Literature

NPL 1: Masao Hiraishi et al., "Synthesis of Highly Ordered Cellulose II in vitro using Cellodextrin Phosphorylase." Carbohydrate Research, Vol. 344, (2009) pp. 2468-2473

SUMMARY OF INVENTION

Technical Problem

In general, an enzyme catalyzes a biochemical reaction in an aqueous solution, and is easily denatured and inactivated in the presence of an organic solvent to lose its catalytic function. Thus, a reaction for enzymatic synthesis of cellooligosaccharides using cellodextrin phosphorylase is conventionally performed in a buffer, using water as a reaction solvent.

However, it was found that when water is used as a reaction solvent, the degree-of-polymerization distribution in cellooligosaccharides is wide, and cellooligosaccharides having a degree of polymerization that is considerably higher than the average degree of polymerization are produced. From the viewpoint of improving the performance of cellooligosaccharides, it may be desirable to suppress the formation of cellooligosaccharides having such a high degree of polymerization, and reduce the degree-of-polymerization distribution.

In view of the above, an object of an embodiment of the present invention is to provide a method that enables suppression of formation of cellooligosaccharides with a high degree of polymerization in enzymatic synthesis of cellooligosaccharides.

Solution to Problem

The method for producing a cellooligosaccharide according to an embodiment of the present invention comprises reacting α-glucose-1-phosphate and at least one primer selected from the group consisting of glucose, cellobiose, and alkylated glucose with cellodextrin phosphorylase in a mixed solvent containing water and a water-soluble organic solvent.

Advantageous Effects of Invention

According to an embodiment of the present invention, the use of a mixed solvent containing a water-soluble organic solvent as a reaction solvent in enzymatic synthesis of cellooligosaccharides using cellodextrin phosphorylase suppresses the formation of cellooligosaccharides having a high degree of polymerization, and enables synthesis of cellooligosaccharides with a narrow degree-of-polymerization distribution.

DESCRIPTION OF EMBODIMENTS

Figure 1:
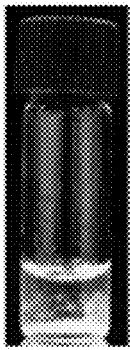
FIG. 1 is photographs showing the solution state after an enzymatic reaction in a test of addition of an organic solvent to a glucose primer synthesis system.

The method for producing a cellooligosaccharide according to the present embodiment comprises reacting α-glucose-1-phosphate (hereinafter also referred to as "αG1P") and at least one primer selected from the group consisting of glucose, cellobiose, and alkylated glucose with cellodextrin phosphorylase (hereinafter also referred to as "CDP"), in a mixed solvent containing water and a water-soluble organic solvent.

This reaction is a synthesis method using the reverse reaction of CDP. αG1P is used as a glucose donor, and at least one member selected from the group consisting of glucose, cellobiose, and alkylated glucose is used as a primer (i.e., a glucose acceptor); and these are reacted with CDP to sequentially polymerize αG1P as a monomer with respect to the primer.

For example, when the primer is glucose, the reaction is as follows.

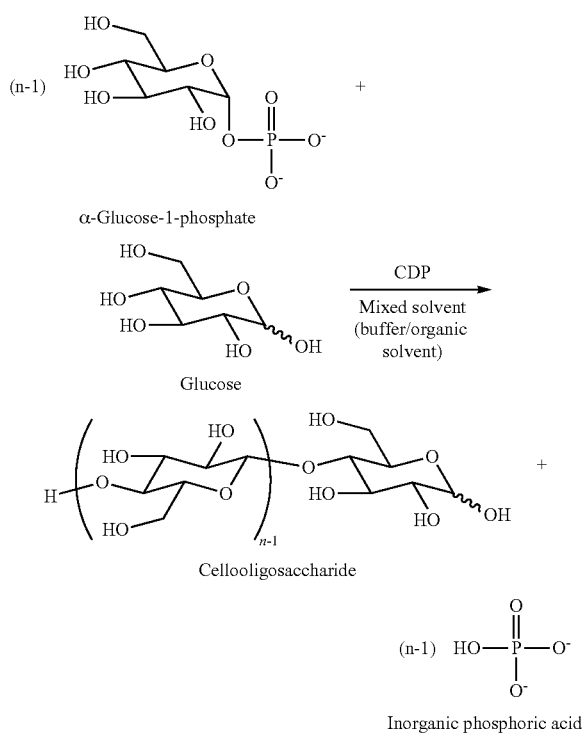

When the primer is cellobiose, the reaction is as follows.

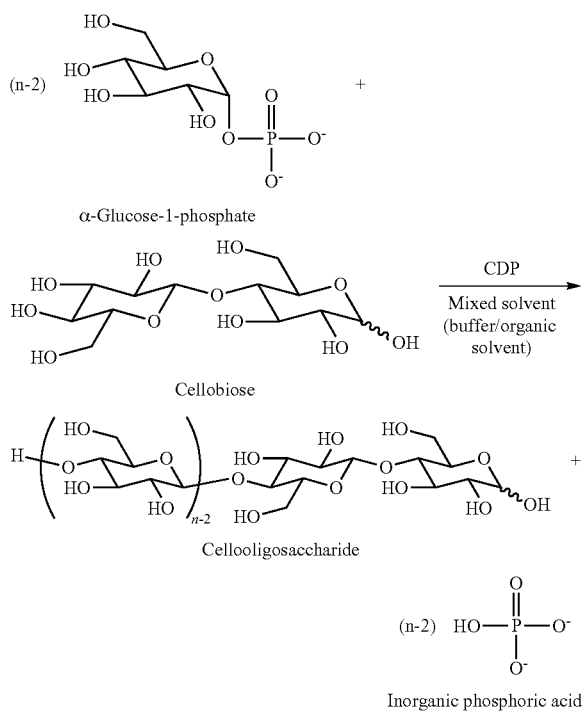

When the primer is alkylated glucose, the reaction is as follows.

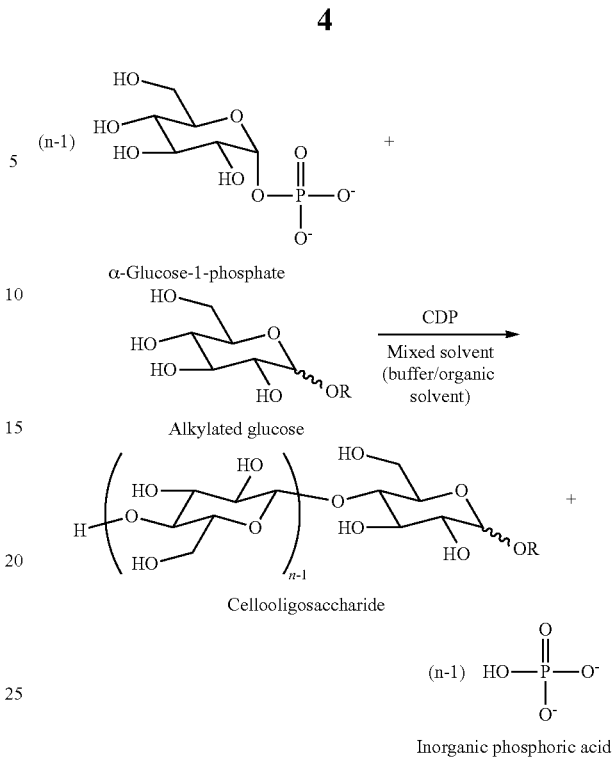

In the above reaction schemes, n is an integer, and indicates the degree of polymerization in the cellooligosaccharide; and R represents an alkyl group.

The alkyl group in the alkylated glucose is, for example, a $C_{1-12}$ alkyl group. The alkyl group R in the above reaction scheme preferably has 1 to 12 carbon atoms. Specific examples include ethyl glucoside, octyl glucoside, decyl glucoside, dodecyl glucoside, and the like.

CDP is known to be produced by microorganisms such as *Clostridium thermocellum*, and microorganisms of the genus *Cellulomonas*; and can be obtained using these microorganisms by a known method. For CDP, for example, CDP derived from *Clostridium thermocellum* YM4 can be prepared by an *Escherichia coli* expression system in accordance with the method described in M. Krishnareddy et al., J. Appl. Glycosci., 2002, 49, 1-8.

The enzyme amount of CDP can be determined, for example, by incubating αG1P, cellobiose, and CDP; quantifying phosphoric acid produced by CDP; and defining the amount of enzyme that liberates 1 μmol of phosphoric acid per minute as 1U.

In the present embodiment, the enzymatic synthesis of cellooligosaccharides using CDP has a feature in that a mixed solvent containing water and a water-soluble organic solvent is used as a reaction solvent. The mixed solvent is a solvent obtained by mixing water and a water-soluble organic solvent; and is generally obtained by mixing a buffer, which is an aqueous solution, and a water-soluble organic solvent.

The water-soluble organic solvent is an organic solvent with a solubility of 5 mL or more in 100 mL of water at 20° C. Examples include $C_{1-4}$ alcohols, such as methanol, ethanol, 1-propanol, isopropyl alcohol, and t-butanol; ketones, such as acetone; ethers, such as tetrahydrofuran; amides, such as N,N-dimethylformamide, N,N-dimethylacetamide, and N-methylpyrrolidone; nitriles, such as acetonitrile; sulfoxides, such as dimethyl sulfoxide; and the like. These may be used singly, or in a combination of two or more. As the water-soluble organic solvent, at least one member selected from the group consisting of methanol (MeOH), ethanol (EtOH), N,N-dimethylformamide (DMF), and dimethyl sulfoxide (DMSO) is more preferably used.

The buffer to be mixed with the water-soluble organic solvent is not particularly limited. Examples include HEPES buffers, Tris-HCl buffers, MOPS buffers, acetate buffers, phosphate buffers, and the like. A buffer that can maintain the pH of the reaction solvent at about 5 to 9 at the reaction temperature is preferably used.

The ratio of water and the water-soluble organic solvent is not particularly limited. Based on the mixed solvent taken as 100 volume %, the amount of the water-soluble organic solvent is preferably 5 to 50 volume %, more preferably 5 to 40 volume %, and even more preferably 5 to 30 volume %; and may be 10 to 25 volume % or 10 to 20 volume %.

The reaction conditions are not particularly limited, and are preferably as follows. The concentration of αG1P is preferably 10 to 1000 mM, and more preferably 100 to 300 mM. The concentration of the primer (glucose, cellobiose, alkylated glucose) is preferably 10 to 200 mM, and more preferably 30 to 70 mM. The concentration of CDP is preferably 0.01 to 1.5 U/mL, and more preferably 0.05 to 0.5 U/mL. The concentration of the buffer (for example, the concentration of HEPES in an HEPES buffer) is preferably 100 to 1000 mM, and more preferably 250 to 750 WM. The reaction temperature may be 10 to 80° C. or 20 to 70° C. The reaction time may be 1 hour to 15 days or 1 to 10 days.

After the completion of the reaction, a reaction liquid containing cellooligosaccharides can be obtained. Since the reaction liquid contains CDP, which is an enzyme, the primer, etc., washing may be performed to remove them. The washing can be performed by repeating the process of separating the precipitate from the supernatant by centrifugation and redispersing the precipitate using a washing solvent, thereby obtaining the cellooligosaccharides. As the washing solvent, a mixed solvent containing water and a water-soluble organic solvent as in the reaction solvent may be used; or water may be used. The cellooligosaccharides are obtained as the precipitate (precipitated product). The cellooligosaccharides are also contained in the supernatant; therefore, the cellooligosaccharides can also be obtained by recovering the product in the supernatant.

The resulting cellooligosaccharides are oligosaccharides with a structure in which glucose is linked by a β-1,4 glycosidic bond. The degree of polymerization (i.e., n in the above reaction schemes) in the cellooligosaccharides may be, for example, 4 or more, 5 or more, or 6 or more; and may also be, for example, 15 or less, 13 or less, or 11 or less. The average degree of polymerization (DP) is not particularly limited. The average degree of polymerization (DP) may be, for example, 5.5 or more, 6.0 or more, or 6.3 or more; and may also be, for example, 9.0 or less, 8.5 or less, or 8.3 or less.

The cellooligosaccharides obtained in the present embodiment may be non-alkylated, as in the case of synthesis using glucose or cellobiose as a primer; or may be alkylated, as in the case of synthesis using alkylated glucose as a primer. That is, the cellooligosaccharides according to the present embodiment encompass cellooligosaccharide derivatives, such as alkylated cellooligosaccharides. The cellooligosaccharides according to the present embodiment also naturally encompass alkali metal ion adducts, such as sodium ion adducts and potassium ion adducts. After synthesis using alkylated glucose as a primer, the alkyl group may be hydrolyzed by a known method to produce non-alkylated cellooligosaccharides.

According to the present embodiment, using a mixed solvent of water and a water-soluble organic solvent as a reaction solvent in enzymatic synthesis of cellooligosaccharides using CUP suppresses the formation of cellooligosaccharides with a high degree of polymerization, and enables cellooligosaccharides with a relatively low degree of polymerization to be selectively obtained.

The use of cellobiose as a primer allows higher selectivity for the degree of polymerization in the product and a narrower degree-of-polymerization distribution than with the use of glucose as a primer. The reason therefor, which is not intended to be a limitation, may be that cellobiose shows a more uniform time to the initiation of a reaction between enzymes.

The application of the cellooligosaccharides according to the present embodiment is not particularly limited; and can be used for various known applications, such as in the pharmaceutical field.

EXAMPLES

Examples are given below to illustrate the present invention in more detail; however, the present invention is not limited to these Examples.
1. Experimental Method
1-1. Reagents LB-Broth Lennox and LB-Agar Lennox were purchased from Funakoshi Co., Ltd. Glycerol, kanamycin sulfate, isopropyl-β-D(−)-thiogalactopyranoside (IPTG), N,N,N',N'-tetramethylethylenediamine (TEMED), dithiothreitol (DTT), 1-butanol, αG1P disodium salt n-hydrate, and 40% sodium deuteroxide solution in D2O were purchased from Wako Pure Chemical Industries, Ltd.

D-(+)-cellobiose was purchased from Nacalai Tesque, Inc.

Nickel-nitrilotriacetic acid (Ni-NTA) agarose gel was purchased from QIAGEN. Protein Molecular Weight Marker (Broad) was purchased from Takara Bio Inc.

Acrylamide, N,N'-methylenebisacrylamide, sodium dodecyl sulfate (SDS), amnonium persulfate (APS), heavy water, 2,5-dihydroxybenzoic acid (DHBA), ProteoMass™ Bradykinin fragment 1-7 MALDI-MS Standard (Bradykinin), ProteoMass™ $P_{14}R$ MALDI-MS Standard ($P_{14}R$), ProteoMass™ ACTH Fragment 18-39 MALDI-MS Standard (ACTH), trifluoroacetic acid (TFA), and acetonitrile were purchased from Sigma-Aldrich.

Other reagents were purchased from Nacalai Tesque, Inc. unless otherwise specified, and reagents of a special grade or higher were used.

As ultrapure water, water purified with Milli-Q system (Milli-Q Advantage A-10, Merck Millipore) was used. As pure water, water purified with TANK 60 Lite PE (Merck Millipore) was used.
1-2. Preparation of Cellodextrin Phosphorylase (CDP) and Enzyme Activity Evaluation CDP was prepared in the same manner as in the method described in M. Krishnareddy et al., J. Appl. Glycosci., 2002, 49, 1-8. The details are as follows.
1-2-1. Preparation of Reagents
(1) Sterile Purified Water 500 mL of ultrapure water was placed in a 500-mL wide-mouth medium bottle, autoclaved (121° C., 20 minutes, BS-245, TOMY), and stored at room temperature.
(2) 50 mg/mL Kanamycin Stock Solution 1.5 g of kanamycin sulfate was dissolved in sterile purified water, and the total volume was adjusted to 30 mL. The prepared solution was sterilized by filtration through a 0.22-μm polyvinylidene fluoride (PVDF) filter in a clean bench. 1 mL of the resulting solution was dispensed into each 1.7 mL tube, and stored at −20° C.

(3) 10 mM IPTG Stock Solution 71.5 mg of IPTG was dissolved in sterile purified water, and the total volume was adjusted to 30 mL. The prepared solution was sterilized by filtration through a 0.22-μm PVDF filter in a clean bench. 1 mL of the resulting solution was dispensed into each 1.7 mL tube, and stored at −20° C.

(4) LB-Agar/Kanamycin Plate 2.8 g of LB-Agar Lennox was placed in a 250-mL wide-mouth medium bottle and dissolved by adding 80 mL of ultrapure water, followed by autoclaving. After cooling to 60° C. or lower at room temperature, 80 μL of the 50 mg/mL kanamycin stock solution was added, followed by mixing, in a clean bench. The resulting mixture was dispensed into sterile petri dishes, allowed to solidify at room temperature, and stored at 4° C. This was used within one month after preparation.

(5) 50% Glycerol Solution 50 mL of glycerol and 50 mL of ultrapure water were placed and mixed in a 250-mL wide-mouth medium bottle. The resulting mixture was autoclaved, and stored at room temperature.

(6) LB Medium 10 g of LB-Broth Lennox was dissolved in 500 mL of pure water in a 500-mL wide-mouth medium bottle, autoclaved, and stored at room temperature.

(7) MOPS-Na Buffer (20 mM, pH 7.5)

4.18 g of 3-morpholinopropane sulfonic acid (MOPS) was dissolved in about 600 mL of ultrapure water. After the pH was adjusted to 7.5 with a 4N sodium hydroxide aqueous solution, the total volume was adjusted to 1 L. The resulting solution was sterilized by filtration through a 0.10-μm PVDF filter, and stored at 4° C.

(8) 70% Ethanol (Biotechnology Grade)

140 mL of ethanol (biotechnology grade) and 60 mL of ultrapure water were placed and mixed in a 250-mL wide-mouth medium bottle, and then stored at room temperature.

(9) Wash Buffer (20 mM MOPS, 300 mM NaCl, 10 mM Imidazole, pH 7.5)

2.09 g of MOPS, 8.77 g of sodium chloride, and 340 mg of imidazole were dissolved in about 350 mL of ultrapure water. After the pH was adjusted to 7.5 with a 4N sodium hydroxide aqueous solution, the total volume was adjusted to 500 mL. The resulting solution was sterilized by filtration through a 0.10-μm PVDF filter, and stored at 4° C.

(10) Elution Buffer (20 mM MOPS, 300 mM NaCl, 250 mM Imidazole, pH 7.5)

2.09 g of MOPS, 8.77 g of sodium chloride, and 8.51 g of imidazole were dissolved in about 350 mL of ultrapure water. After the pH was adjusted to 7.5 with a 4N sodium hydroxide aqueous solution, the total volume was adjusted to 500 mL. The resulting solution was sterilized by filtration through a 0.10-μm PVDF filter, and stored at 4° C.

(11) 5% (w/v) Sodium Azide Stock Solution 500 mg of sodium azide was weighed using a plastic spatula and dissolved by adding a MOPS-Na buffer (20 mM, pH 7.5) so that the total volume was 10 mL, and the resulting solution was stored at 4° C. with protection from light.

(12) 30% Acrylamide/Bis Mixed Solution 29.2 g of acrylamide and 0.8 g of N,N'-methylenebisacrylamide were dissolved in about 70 mL of ultrapure water with stirring. The total volume was adjusted to 100 mL, and the resulting solution was stored at 4° C. with protection from light.

(13) Tris-HCl Buffer (1.5 M, pH 8.8)

18.17 g of tris(hydroxymethyl)aminomethane (Tris) was dissolved in about 80 mL of ultrapure water with stirring. After the pH was adjusted to 8.8 with 6N hydrochloric acid, the total volume was adjusted to 100 mL. The resulting solution was stored at 4° C.

(14) Tris-HCl Buffer (0.5 M, pH 6.8)

6.06 g of Tris was dissolved in about 80 mL of ultrapure water with stirring. After the pH was adjusted to 6.8 with 6N hydrochloric acid, the total volume was adjusted to 100 mL. The resulting solution was stored at 4° C.

(15) 10% SDS Aqueous Solution 10 g of sodium dodecyl sulfate (SDS) was dissolved in about 90 mL of ultrapure water with stirring. The total volume was adjusted to 100 mL, and the resulting solution was stored at room temperature.

(16) 10% APS Aqueous Solution 0.1 g of ammonium persulfate (APS) was dissolved in about 1 mL of ultrapure water, and the resulting solution was stored at 4° C.

(17) Saturated 1-Butanol 1-butanol and ultrapure water were mixed at a ratio of 2:1, and stored at room temperature.

(18) 5× Running Buffer (125 mM Tris, 960 mM Glycine, 0.5% SDS)

15.1 g of Tris, 72.1 g of glycine, and 5.0 g of SDS were dissolved in ultrapure water so that the total volume was 1 L, and the resulting solution was stored at 4° C. and diluted 5-fold with ultrapure water when used. The running buffer after a single use was collected and reused, and the number of times of use was set to a maximum of 2 times.

(19) 5× Loading Buffer (200 mM Tris, 0.05% Bromophenol Blue, 10% SDS, 50% Glycerol)

2.42 g of Tris, 10.0 g of SDS, and 50 mg of bromophenol blue were dissolved by adding 50 mL of glycerol and about 40 mL of ultrapure water. After the pH was adjusted to 6.8 with 6N hydrochloric acid, the total volume was adjusted to 100 mL. 1 mL of the resulting solution was dispensed into each 1.7-mL tube, and stored at 4° C.

(20) 1M DTT Solution

About 150 mg of dithiothreitol (DTT) was dissolved by adding about 1 mL of ultrapure water so that the concentration was 1 M, and the resulting solution was stored at −20° C.

(21) Fixation Solution

After 50 mL of acetic acid and 200 mL of ethanol were mixed, ultrapure water was added to make a total volume of 500 mL, and the resulting solution was stored at room temperature.

(22) Destaining Solution

After 40 mL of acetic acid and 125 mL of ethanol were mixed, ultrapure water was added to make a total volume of 500 mL, and the resulting solution was stored at room temperature.

(23) Staining Solution 0.25 g of Coomassie Brilliant Blue R-250 was added to 100 mL of the destaining solution and dissolved with stirring, and the resulting solution was stored at room temperature with protection from light.

1-2-2. Culturing of *Escherichia coli* and Expression of CDP (1) Preparation of *E. coli* BL21-CDP Glycerol Stock From a glycerol stock of *Escherichia coli* BL21-Gold (DE3) strain (*E. coli* BL21-CDP) having a plasmid containing the gene of CDP derived from *Clostridium thermocellum* YM4, *E. coli* BL21-CDP was inoculated on an LB-Agar/kanamycin plate using a platinum loop that had been sterilized by heating with a gas burner and allowed to cool; and cultured at 37° C. for 8 to 12 hours. After a mixed solution of 5 µL of a 50 mg/mL kanamycin stock solution and 5 mL of an LB medium was added to a test tube pre-sterilized by dry heat, *E. coli* BL21-CDP was inoculated from a single colony using a heated platinum loop. Shaking culture (reciprocation, 200 rpm) was performed at 37° C. using a shaker incubator (BR-23FP, TAITEC) until the $OD_{660}$ reached 0.6 to 0.8. Thereafter, 800 µL of the culture medium was collected in a 1.7-mL tube and mixed with 100 µL of a 50% glycerol solution. The resulting mixture was frozen with liquid nitrogen, and stored at −80° C.

(2) Preparation of *E. coli* BL21-CDP Master Plate

From the glycerol stock of *E. coli* BL21-CDP or a master plate within 1 month after preparation, *E. coli* BL21-CDP was inoculated on an LB-Agar/kanamycin plate using a platinum loop that had been sterilized by heating with a gas burner and allowed to cool; and cultured at 37° C. for 8 to 12 hours. The resulting plate was stored at 4° C. when *E. coli* BL21-CDP was inoculated from the master plate. When *E. coli* BL21-CDP was inoculated from the glycerol stock, inoculation on an LB-Agar/kanamycin plate was further performed, followed by culturing at 37° C. for 8 to 12 hours; and the resulting plate was stored at 4° C.

(3) Preparation of *E. coli* BL21-CDP Pre-Culture 3 mL of an LB medium was placed in a test tube sterilized by dry heat, and 3 µL of a 50 mg/mL kanamycin stock solution was added. *E. coli* BL21-CDP was inoculated from a single colony of the *E. coli* BL21-CDP master plate using a platinum loop that had been sterilized by heating and allowed to cool. Shaking culture (reciprocation, 200 rpm) was performed at 37° C. for 10 to 12 hours using a shaker incubator.

(4) Culturing of *E. coli* BL21-CDP and Expression of CDP

After 6 g of LB-Broth Lennox was weighed in each of two 1-L baffled flasks, 300 mL of pure water was added, and the flasks were autoclaved and allowed to cool. 300 µL of a 50 mg/mL kanamycin stock solution was added to each flask, followed by mixing. Thereafter, 300 L of the *E. coli* BL21-CDP pre-culture was added. Shaking culture (rotation, 600 rpm) was performed at 30° C. using a shaker incubator. After it was confirmed that the $OD_{600}$ reached 0.55 to 0.60, 3 mL of a 10 mM IPTG stock solution was added to each flask. Shaking culture (rotation, 200 rpm) was performed at 25° C. for 20 hours to express CDP.

1-2-3. His-Tag Purification and Buffer Replacement (1) Extraction of CDP by Disrupting *E. coli* BL21-CDP About 50 mL of the *E. coli* BL21-CDP suspension prepared in Item 1-2-2 (4) above, in which CDP was expressed, was equally dispensed into each of 12 50-mL tubes; and subjected to centrifugation (3500 rpm, 20 minutes, 4° C.) with a centrifuge (centrifuge: EX-126, TOMY; rotor: 3850-04P, TOMY). The supernatant in each tube was removed by decantation, and a MOPS-Na buffer (20 mM, pH 7.5) was added to the precipitated *E. coli* BL21-CDP pellet to make a total volume of about 15 mL in each tube, followed by vigorous shaking by hand for suspension. About 45 mL of the *E. coli* BL21-CDP suspension was dispensed in each of four 100-mL self-standing tubes, and *E. coli* BL21-CDP was disrupted by ultrasonic irradiation using a probe-type sonicator (Sonifier 250, Branson) in an ice bath. Two cycles of ultrasonic irradiation were performed under the conditions of power: 200 W (dial 10) and duty cycle: 30%, wherein four repetitions of 5-second ultrasonic irradiation and a 25-second interval was regarded as one cycle. After that, the *E. coli* disruption liquid was always in an ice bath to prevent decomposition of CDP by a protease or the like in the *E. coli* BL21-CDP disruption liquid. The *E. coli* BL21-CDP disruption liquid in each of the four 100-mL tubes was individually transferred to a 50-mL tube, and centrifuged (3500 rpm, >20 minutes, 4° C.). Thereafter, the supernatant in each tube was individually collected in a 50-mL tube by decantation.

(2) Purification of CDP Using Ni-NTA Affinity Column 9.8 mL of an Ni-NTA agarose gel (GE Healthcare) dispersion was placed in a plastic column (1.8 cm in diameter and 10 cm in length) that had been sterilized with 70% ethanol and subjected beforehand to replacement by ultrapure water. The NI-NTA agarose gel was sterilized and washed by filling the column with 70% ethanol, and allowing it to flow. This operation was repeated twice. 3 mL of a MOPS-Na buffer (20 mM, pH 7.5) was applied and allowed to flow, and 3 mL of the buffer was further applied. The Ni-NTA agarose gel was redispersed by stirring with a spatula to remove air bubbles, followed by replacement by 5 mL of a MOPS-Na buffer (20 mM, pH 7.5) four times.

The supernatant of the *E. coli* BL21-CDP disruption liquid was applied to the column, and the solution flowing from the column was collected and used as a flow-through solution. 3 to 5 mL of a wash buffer was applied for replacement, and 3 to 5 mL of the wash buffer was further applied. After the Ni-NTA agarose gel was redispersed by pipetting to make the surface of the gel layer uniform, the applied wash buffer was allowed to flow. Further, the operation of applying 5 mL of the wash buffer for replacement was repeated so that the wash buffer was applied in a total amount of 30 mL or more. All of the solutions that passed through when the wash buffer was applied were collected and used as a wash solution. Thereafter, 3 to 5 mL of an elution buffer was applied, and 1 mL fractions were collected in 1.7-mL tubes as an eluate. This operation was repeated so that the elution buffer was applied in a total amount of 25 mL. The absorbance of each fraction was measured with a microvolume ultraviolet-visible spectrophotometer (NanoDrop 2000c, Thermo Scientific), and protein elution was confirmed using the absorbance at 280 nm as an index. In this case, ultrapure water was used for background measurement. When protein elution was not completed, the elution buffer was applied to the column until no absorption at 280 nm was observed. In the collected eluate, a fraction with high absorbance was collected and used as a CDP solution.

(3) Buffer Replacement for CDP Solution

Buffer replacement for the CDP solution was performed using PD10 columns (Sephadex G-25, GE Healthcare) according to the accompanying instructions. The required number of PD10 columns was used according to the volume of the CDP solution. The PD10 columns were fixed to 50-mL tubes using the supplied adapters. The PD10 columns were filled with 70% ethanol, and centrifuged (1000 g, 2 minutes, 4° C.) using a centrifuge (MX-305, TOMY). The columns were sterilized and washed by repeating this operation twice. The operation of filling the columns with a 0.02% sodium azide/20 mM MOPS-Na buffer prepared by diluting a 5% (w/v) sodium azide stock solution 250-fold with a MOPS-Na buffer (20 mM, pH 7.5) and allowing the solution to flow by allowing it to stand was repeated four times to perform buffer replacement in the PD10 columns. Further, the 0.02% sodium azide/20 mM MOPS-Na buffer was added, followed by centrifugation.

The PD10 columns were transferred into new 50-mL tubes, and 1.75 to 2.5 mL of the CDP solution was applied to each of the PD10 columns so that the slope of Sephadex was not broken by centrifugation. The columns were fixed in a centrifuge at the same angle as in the centrifugation described above, and centrifuged. The eluted solution was collected and used as a CDP stock solution. The absorbance at 280 nm of the CDP stock solution was measured with a NanoDrop 2000c, and 1 mL of the CDP stock solution was dispensed into each 1.7-mL tube and stored at 4° C.

30 mL of a MOPS-Na buffer (20 mM, pH 7.5) was added to each of the columns, and allowed to stand to wash the columns. Subsequently, the operation of filing the columns with ultrapure water and performing centrifugation was repeated twice. The columns were also washed with a 50 volume % ethanol aqueous solution twice. The PD10 columns were filled with a 50 volume % ethanol aqueous solution, and stored at 4° C.

1-2-4. Confirmation of Purification of CDP by Polyacrylamide Gel Electrophoresis (SDS-PAGE)

(1) Preparation of 10% Acrylamide Gel 3.33 mL of a 30% acrylamide/bis mixed solution, 2.5 mL of a Tris-HCl buffer (1.5 M, pH 8.8), and 4.01 mL of ultrapure water were placed in a 50-mL tube; and degassed by aspiration with an aspirator under ultrasonic irradiation. 100 µL of a 10% SDS aqueous solution, 50 µL of a 10% APS aqueous solution, and 10 µL of TEMED were added and mixed by pipetting so as to avoid foaming. 3.5 mL of the mixed solution was added to the gap (0.75 mm) between two glass plates, gently overlaid with 900 µL of saturated 1-butanol, and allowed to stand at room temperature for 1 hour for polymerization. The saturated 1-butanol was removed using a micropipette, and then washed with ultrapure water to obtain a separation gel.

0.44 mL of a 30% acrylamide/bis mixed solution, 0.44 mL of a Tris-HCl buffer (0.5 M, pH 6.8), and 2.03 mL of ultrapure water were placed in a 50-mL tube and degassed by aspiration with an aspirator under ultrasonic irradiation. 33 µL of a 10% SDS aqueous solution, 16.7 µL of a 10% APS aqueous solution, and 1.65 µL of TEMED were added and mixed by pipetting so as to avoid foaming. The solution was sufficiently added on the separation gel; and a 10-well comb was carefully set so as to prevent air from entering, followed by being allowed to stand at room temperature for 1 hour for polymerization. The resulting gel, together with the glass plates, was placed between sufficiently moistened Kimwipes, wrapped in plastic wrap, and stored at 4° C.

(2) Evaluation by Electrophoresis

5 µL of Protein Molecular Weight Marker (Broad), 2 µL of a 1 M DTT solution, 20 µL of a 5× loading buffer, and 173 µL of sterile purified water were placed and mixed in a 1.7-mL tube; and the resulting mixture was stored as a marker at −20° C. The CDP stock solution, and the flow-through solution and the wash solution, both of which were collected in purification of CDP, were each individually mixed in an amount of 1 µL with 2 µL of a 5× loading buffer, 1 µL of 1 M DTT, and 6 µL of ultrapure water. The resulting mixtures and 10 µL of the marker thawed at room temperature were subjected to heat treatment at 105° C., and spun down with a tabletop small-sized centrifuge (R5-AQBD02, Recenttec). The polyacrylamide gel prepared in Item (1) above was set in a container for electrophoresis (Mini-PROTEAN Tetra cell, Bio-Rad), 500 mL of a 5× running buffer diluted 5-fold with ultrapure water was poured, and the comb was removed. Each of the electrophoresis samples was individually loaded in an individual well, and electrophoresed at a voltage of 150 V for about 40 minutes using an electrophoresis device (Mini-PROTEAN Tetra system, Bio-Rad). When the band reached about 1 cm above the lower end of the gel, the electrophoresis was stopped; and the gel was removed from the glass plates, immersed in a fixation solution, and shaken with a shaker (Wave-PR, TAITECH) for 30 minutes with protection from light. The fixation solution was removed, and the gel was immersed in a staining solution and shaken for 60 minutes with protection from light. The staining solution was collected, and the gel was immersed in a destaining solution and shaken for 30 minutes with protection from light. The operation of removing the destaining solution, newly adding a destaining solution, and shaking was repeated until the bands of the proteins contained in the marker were clearly visible. The gel was washed with ultrapure water, photographed with Gel Doc EZ Imager (Bio-Rad), and analyzed using the accompanying software.

1-2-5. Measurement of Enzyme Activity of CDP

D-(+)-cellobiose was dissolved in ultrapure water to 300 mM, and used as a cellobiose stock solution. The activity of CDP was measured in the following manner. A 3-morpholinopropane sulfonic acid buffer (50 m4, pH 7.5) containing $\alpha$G1P (50 mM), D-(+)-cellobiose (50 mM) and CDP diluted at a predetermined ratio was incubated at 37° C. The amount of phosphoric acid produced by CDP was quantified, and the enzyme activity (U/mL) when the amount of enzyme that liberates 1 µmol of phosphoric acid per minute was defined as 1U was determined. The CDP dilution ratio was determined so that the conversion of $\alpha$G1P was 10% or less when the reaction time was 100 minutes.

1-3. Enzymatic Synthesis of Cellooligosaccharide 1-3-1. Enzymatic Synthesis of Cellooligosaccharide by CDP (Primer: Glucose)

23.8 g of 2-[4-(2-hydroxyethyl)-1-piperazinyl]ethanesulfonic acid (HEPES) was dissolved in about 60 mL of ultrapure water. After the pH was adjusted to 7.5 with a 4N sodium hydroxide aqueous solution, the total volume was adjusted to 100 mL, followed by sterilization by filtration through a 0.22-µm PVDF filter. The resulting solution was stored at 4° C. as an HEPES buffer (1 M, pH 7.5).

D-(+)-glucose and $\alpha$G1P disodium salt n-hydrate were weighed in predetermined amounts and individually dissolved in ultrapure water to 1 M to obtain a 1 M glucose stock solution and 1 M $\alpha$G1P aqueous solution.

The HEPES buffer, the 1 M $\alpha$G1P aqueous solution, and the 1 M glucose stock solution were placed in a 4-mL tube so that the concentrations thereof during reaction were 500 mM, 200 mM, and 50 mM, respectively; and a predetermined amount of methanol (MeOH), ethanol (EtOH), N,N-dimethylformamide (DMF), or dimethyl sulfoxide (DMSO) was added as a water-soluble organic solvent. The total volume was adjusted with ultrapure water, taking into account the amount of the CDP stock solution to be used, and degassed by aspiration with an aspirator under ultrasonic irradiation. An appropriate amount of the CDP stock solution was added so that the final concentration was 0.2 U/mL, followed by mixing by pipetting so as to prevent air bubbles. The resulting mixture was aliquoted in a predetermined amount into 1.7-mL tubes or 1-mL Mighty vials, and incubated at 60° C. for 3 days.

Regarding mixed solvents as reaction solvents, an HEPES buffer (500 mM, pH 7.5) containing 10 volume % MeOH is denoted as 10% MeOH (i.e., the mixed solvent contains 10 volume % MeOH). Other mixed solvents are also denoted in the same manner. A control in which incubation was performed in the same manner, except that no water-soluble organic solvent was added, was denoted as "(−)."

1-3-2. Enzymatic Synthesis of Cellooligosaccharide by CDP (Primer: Cellobiose)

A reaction for enzymatic synthesis of cellooligosaccharides was performed in the same manner as in Item 1-3-1, except that the 300 mM cellobiose stock solution was used in place of the 1 M glucose stock solution.

1-3-3. Enzymatic Synthesis of Cellooligosaccharide by CDP (Primer: Alkylated Glucose)

A reaction for enzymatic synthesis of cellooligosaccharides was performed in the same manner as in Item 1-3-1, except that a 300 mM ethyl glucoside stock solution or a 300 mM octyl glucoside stock solution was used in place of the 1 M glucose stock solution. The 300 mM ethyl glucoside stock solution and the 300 mM octyl glucoside stock solution were prepared by weighing ethyl β-D-glucoside (Carbosynth Limited) and n-octyl-β-glucoside (Dojindo Laboratories) in predetermined amounts, and individually dissolving each of them in ultrapure water to 300 mM.

1-3-4. Purification of Enzymatically Synthesized Cellooligosaccharide

To use the products prepared in Items 1-3-1 to 1-3-3 for various analyses, the products were purified using ultrapure water, or a mixed solvent of ultrapure water and an organic solvent as a washing solvent. Specifically, a washing solvent was added; each product was mechanically disrupted and dispersed by water flow generated by pipetting, and centrifuged (15000 rpm, 10 minutes or more, 4° C.); and the supernatant was removed. The operation of redispersing the precipitate by diluting it 10-fold by adding a washing solvent and performing centrifugation was repeated five times, and purification was performed until the solution replacement percentage was 99.999% or more. The purified dispersion was heated with a heat block at 100° C. for 10 minutes to inactivate the remaining CDP. In the controls (−), purification was performed using ultrapure water as a washing solvent.

The yield of each product was calculated by drying the purified aqueous dispersion to a bone-dry state. A sample tube that had been dried at 105° C. for 24 hours and allowed to cool in a desiccator beforehand was weighed, and the purified aqueous dispersion was added and dried at 105° C. for 24 hours. Thereafter, the sample tube was allowed to cool in a desiccator and weighed. The concentration of the product was calculated from the difference in weight before and after drying. This operation was performed simultaneously in triplicate, and the yield of the product was calculated from the average value thereof.

When measurement by matrix-assisted laser desorption/ionization time-of-flight mass spectrometry (MALDI-TOF-MS) was used, the purified dispersion was diluted with ultrapure water and used.

1-4. Evaluation of Properties of Enzymatically Synthesized Cellooligosaccharide 1-4-1. Inversion Test of Product The gelation of samples prepared using 1-mL Mighty vials was evaluated by an inversion test. Each vial was inverted, and allowed to stand. When the product did not flow, it was determined that a gel-like structure was formed.

1-4-2. Evaluation of Chemical Structure of Product (1) Measurement of Yield of Product The yield was calculated by drying to a bone-dry state by the method indicated in Item 1-3-4.

(2) MALDI-TOF-MS Measurement of Product

The standard sample used for calibration of mass-to-charge ratio was prepared by mixing a Bradykinin fragment 1-7 aqueous solution (10 nmol/mL Bradykinin fragment 1-7, 0.05 mass % trifluoroacetic acid (TFA), 50 mass % acetonitrile), a $P_{14}R$ aqueous solution (10 nmol/mL PAR, 0.1 mass % TFA), and an ACTH fragment 18-39 aqueous solution (10 nmol/mL ACTH fragment 18-39, 0.1 mass % TFA), each in an amount of 5 μL; and 5 μL of a 10 mg/mL DHBA aqueous solution, 1 μL of a 1.0 mass % TFA aqueous solution, and 4 μL of acetonitrile, in a 1.7-mL tube.

The measurement sample of each product was prepared by mixing 1 μL of a 0.1% (w/v) aqueous dispersion of the product, 1 μL of a 10 mg/mL DHBA aqueous solution, and 3 μL of an acetonitrile solution of trifluoroacetic acid (0.2 volume %) in a Mighty vial washed with a methanol solution of potassium hydroxide (3.3 mass %).

The operation of mounting the standard sample and the measurement samples of the products, each in an amount of 1 μL, on a sample plate and air-drying the samples was repeated five times. After vacuum-drying for 1 hour or more, measurement was performed by MALDI-TOF-MS (AXIMA-performance, Shimadzu Corporation). The measurement conditions were Mode: Liner (positive), Mass Range: 1.0-3000.0, Max Leaser Rap Rate: 10, power: 100, profiles: 100, shots: 2, Ion Gate (Da): Blank 500, and Pulsed Extraction optimized at (Da): 1000.0.

The MS spectra obtained by the measurement were processed under the conditions of smoothing method: Gaussian, smoothing filter width: 19, and baseline filter width: 1000.

The peak areas of the sodium ion adducts or the potassium ion adducts were summed, and the peak area of each degree of polymerization was calculated. The average value of the degree of polymerization was calculated from the percentage of the calculated peak area of each degree of polymerization, and defined as the average degree of polymerization. The degree-of-polymerization distribution was evaluated by the standard deviation from the average degree of polymerization by analyzing the MALDI-TOF-MS spectra according to the following equation.

Figure 2:
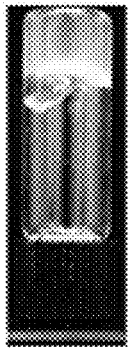
FIG. 2 is photographs showing the solution state after an enzymatic reaction in a test of addition of an organic solvent to a cellobiose primer synthesis system.

Standard deviation=$\sqrt{A/B}$ $A=\Sigma$(each degree of polymerization−average degree of polymerization)$^2$×peak area of each degree of polymerization $B=$sum of peak areas 2. Results and Discussion 2-1. Solution State after Enzymatic Reaction Glucose or cellobiose was used for an enzymatic synthesis system by CDP. Using αG1P as a monomer and glucose or cellobiose as a primer, incubation was performed in HEPES buffers (500 mM, pH 7.5) each individually containing a predetermined concentration of a respective water-soluble organic solvent, at 60° C. for 3 days. As a result, when any of the water-soluble organic solvents was used, the entire solution after the reaction became cloudy, suggesting that the primer was recognized by CDP under the same conditions and that cellooligosaccharides were enzymatically synthesized (see FIG. 1 (glucose primer synthesis system) and FIG. 2 (cellobiose primer synthesis system)). Furthermore, in the case of using 10% EtOH or 20% DMSO as a reaction solvent in the synthesis system using the glucose primer and in the case of using any of the reaction solvents in the synthesis system using the cellobiose primer, the solution did not flow down when the container was inverted, indicating that a gel-like structure was formed.

Figure 3:
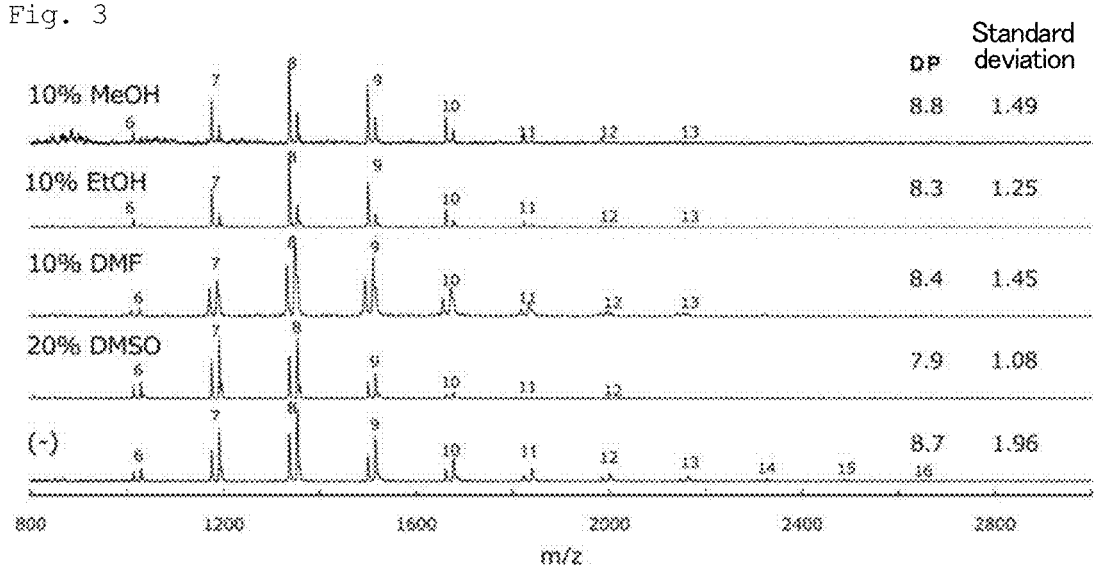
FIG. 3 shows MS spectra of precipitated products in the test of addition of an organic solvent to a glucose primer synthesis system.

2-2. Evaluation of Degree of Polymerization of Enzymatically Synthesized Cellooligosaccharide and Distribution Thereof 2-2-1. Effect of Adding Organic Solvent to Glucose Primer Synthesis System Products enzymatically synthesized in various mixed solvents using a glucose primer were purified using, as a washing solvent, water containing an organic solvent in the same proportion as that of each respective reaction solvent. Thereafter, the precipitated products were subjected to MALDI-TOF-MS spectrum measurement. FIG. 3 shows the obtained MS spectra, all of which show multiple peaks whose m/z spacing corresponds to that of a glucosyl unit (162 Da). Further, each of the detected peaks corresponds to a sodium ion adduct or potassium ion adduct of a cellulose oligomer having a degree of polymerization of about 6 to 16 mers. Thus, the results revealed that cellooligosaccharides having a predetermined degree-of-polymerization distribution were enzymatically synthesized. When the mixed solvents containing a water-soluble organic solvent were used, the average degree of polymerization (DP) was equivalent to or slightly lower than that of the control (−), which was enzymatically synthesized in an HEPES buffer containing no water-soluble organic solvent. Further, the standard deviation was small, and the degree-of-polymerization distribution was narrow. As is clear from FIG. 3, when the mixed solvents were used, the formation of oligomers having a degree of polymerization (n) as high as 14 to 16 was suppressed.

Table 1 shows the results of calculations of the percentage of each degree of polymerization in the case of 10% MeOH, the case of 20% DMSO, and the case of the control (−) from the MS spectrum data of FIG. 3. As is clear from Table 1, when the mixed solvents were used, the formation of oligomers having a high degree of polymerization was suppressed as compared with the control (−). The percentages of a degree of polymerization of 15 and a degree of polymerization of 16 are not shown in Table 1, because they are less than 1%. In Table 1, "0%" means below the detection limit.

TABLE 1

| Reaction solvent | Percentage of each degree of polymerization (%) | | | | | | | | | DP | Standard deviation |
|---|---|---|---|---|---|---|---|---|---|---|---|
| | 6 | 7 | 8 | 9 | 10 | 11 | 12 | 13 | 14 | | |
| 10% MeOH | 2 | 13 | 31 | 28 | 15 | 7 | 2 | 1 | 0 | 8.8 | 1.49 |
| 20% DMSO | 7 | 29 | 39 | 17 | 5 | 1 | 1 | 0 | 0 | 7.9 | 1.08 |
| (—) | 4 | 20 | 31 | 19 | 11 | 5 | 4 | 2 | 1 | 8.7 | 1.96 |

2-2-2. Effect of Adding Organic Solvent to Cellobiose Primer Synthesis System

Figure 4:
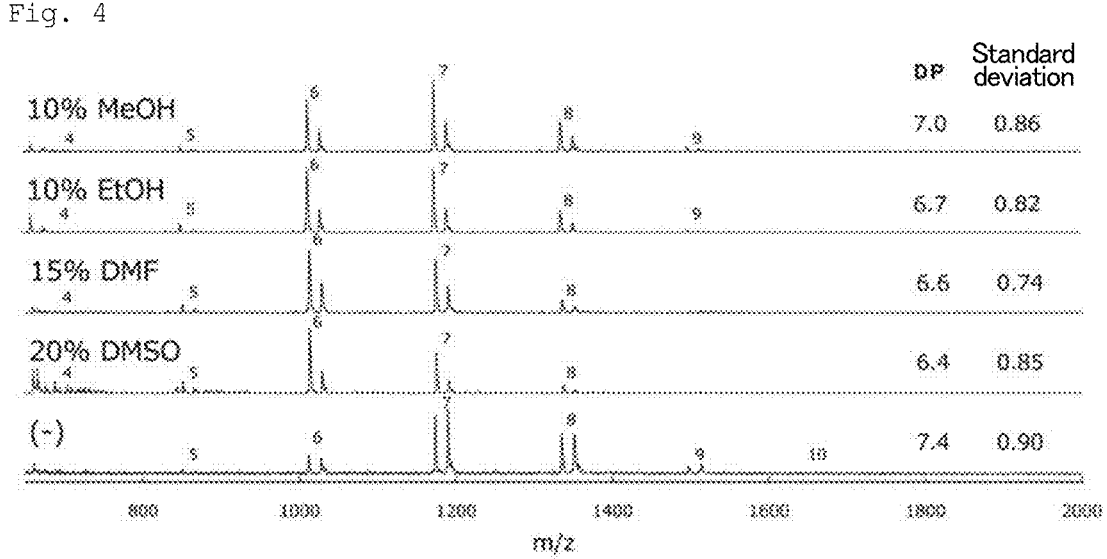
FIG. 4 shows MS spectra of precipitated products in the test of addition of an organic solvent to a cellobiose primer synthesis system.

Products enzymatically synthesized in various mixed solvents using a cellobiose primer were purified using, as a washing solvent, water containing an organic solvent in the same proportion as that of each respective reaction solvent. Thereafter, the precipitated products were subjected to MALDI-TOF-MS spectrum measurement. FIG. 4 shows the obtained MS spectra, all of which show multiple peaks whose m/z spacing corresponds to that of a glucosyl unit. Further, each of the detected peaks corresponds to a sodium ion adduct or potassium ion adduct of a cellulose oligomer having a degree of polymerization of about 4 to 10 mers. Thus, the results revealed that cellooligosaccharides having a predetermined degree-of-polymerization distribution were enzymatically synthesized. Further, as is clear from a comparison with the results in Item 2-2-1, when cellobiose was used as a primer, the degree of polymerization was lower, and the degree-of-polymerization distribution was narrower, than those when glucose was used as a primer; this indicates that higher selectivity for the degree of polymerization was exhibited.

When the mixed solvents containing a water-soluble organic solvent were used, the average degree of polymerization (DP) was slightly lower than that of the control (−), which was enzymatically synthesized in an HEPES buffer containing no water-soluble organic solvent. No significant difference in standard deviation was observed, because the standard deviation in the control (−) was also considerably small. However, as is clear from the MS spectra of FIG. 4, when the mixed solvents were used, the formation of oligomers having a degree of polymerization (n) as high as 8 to 10 was suppressed, as compared with the control (−).

Table 2 shows the results of calculations of the percentage of each degree of polymerization in the case of 10% MeOH, the case of 15% DMF, the case of 20% DMSO, and the case of the control (−) from the MS spectrum data of FIG. 4. As is clear from Table 2, when the mixed solvents were used, the formation of oligomers having a high degree of polymerization (degree of polymerization=8 to 9) was suppressed, as compared with the control (−). This effect was especially high in the case of 15% DMF and the case of 20% DMSO. In Table 2, "0%" means below the detection limit.

The conversion of αG1P, a monomer, was calculated using the yield of each precipitated product calculated by drying to a bone-dry state, and the average degree of polymerization (DP) calculated by MALDI-TOF-MS spectrum measurement. Table 2 shows the results. The conversion of αG1P in the case of 10% MeOH, the case of 15% DMF, the case of 20% DMSO, and the case of the control (−) was 65%, 50%, 60%, and 55%, respectively.

TABLE 2

| Reaction solvent | Percentage of each degree of polymerization (%) | | | | | DP | Standard deviation | Conversion (%) |
|---|---|---|---|---|---|---|---|---|
| | 5 | 6 | 7 | 8 | 9 | | | |
| 10% MeOH | 2 | 25 | 47 | 21 | 3 | 7.0 | 0.86 | 65 |
| 15% DMF | 3 | 47 | 40 | 9 | 1 | 6.6 | 0.74 | 50 |
| 20% DMSO | 7 | 46 | 37 | 7 | 0 | 6.4 | 0.85 | 60 |
| (—) | 2 | 13 | 41 | 35 | 8 | 7.4 | 0.90 | 55 |

2-2-3. Influence of Washing Solvent, and Confirmation of Difference Between Precipitated Product and Product in Supernatant A product enzymatically synthesized in 20% DMSO using a cellobiose primer as in Item 2-2-2 was purified by repeating the operation of centrifugation and redispersion five times using water or 20% DMSO as a washing solvent. The product in the supernatant obtained by mixing the supernatants obtained after the third to fifth centrifugations during the purification, and the precipitated product obtained after the fifth centrifugation were subjected to MALDI-TOF-MS spectrum measurement.

Figure 5:
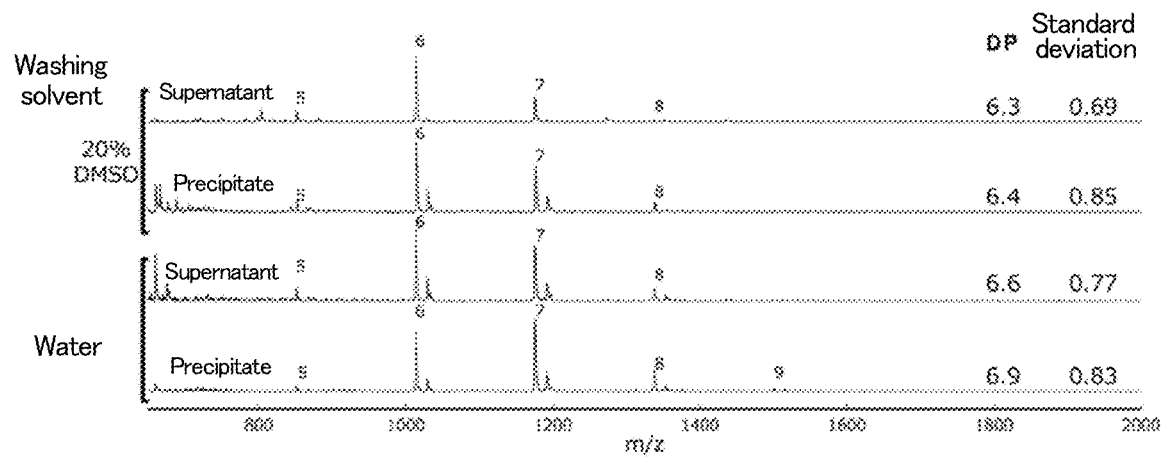
FIG. 5 shows MS spectra of a precipitated product and a product in a supernatant in the case of each of two washing solvents in a cellobiose primer synthesis system.

FIG. 5 shows the results. Almost no difference was observed in the MS spectrum, average degree of polymerization (DP), and standard deviation, depending on the washing solvent. It was thus revealed that the differences in the MS spectrum etc. in Item 2-2-2 were due to the difference in the reaction solvent, rather than due to the washing solvent.

2-2-4. Confirmation of Product in Supernatant

A product enzymatically synthesized in 20% DMSO or 30% DMSO using a cellobiose primer as in Item 2-2-2 was purified by repeating the operation of centrifugation and redispersion five times using, as a washing solvent, water containing DMSO in the same proportion as that of the reaction solvent. In the reaction using 20% DMSO, the product in the supernatant obtained by mixing the supernatants obtained after the third to fifth centrifugations during the purification, and the precipitated product obtained after the fifth centrifugation, were subjected to MALDI-TOF-MS spectrum measurement. In the reaction using 30% DMSO, the product in the supernatant obtained by desalting the supernatant after the first centrifugation during the purification with Millipore ZipTip, and the precipitated product after the fifth centrifugation, were subjected to MALDI-TOF-MS spectrum measurement.

Figure 6:
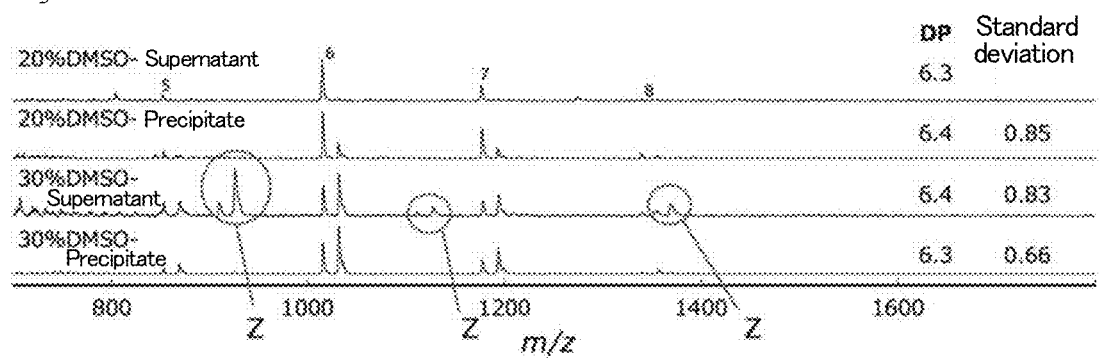
FIG. 6 shows MS spectra of precipitated products and products in supernatants in a cellobiose primer synthesis system.

FIG. 6 shows the results. When 30% DMSO was used as a reaction solvent, the formation of oligomers having a degree of polymerization (n) as high as 8 to 10 was also suppressed, as in the case of 20% DMSO. The peaks indicated by the character Z in FIG. 6 are considered to be impurities derived from ZipTip.

Figure 7:
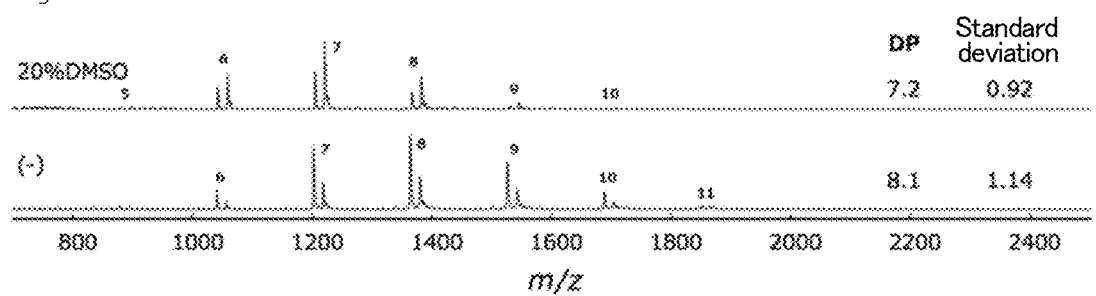
FIG. 7 shows MS spectra of precipitated products in a test of addition of an organic solvent to an ethyl glucoside primer synthesis system.

2-2-5. Effect of Addition of Organic Solvent to Ethyl Glucoside Primer Synthesis System A precipitated product enzymatically synthesized using an ethyl glucoside primer and 20% DMSO as a reaction solvent was purified by repeating the operation of centrifugation and redispersion five times using, as a washing solvent, water containing DMSO in the same proportion as that of the reaction solvent. Thereafter, the resulting precipitated product was subjected to MALDI-TOF-MS spectrum measurement. FIG. 7 shows the obtained MS spectrum, which shows multiple peaks whose m/z spacing corresponds to that of a glucosyl unit. Further, each of the detected peaks corresponds to a sodium ion adduct or potassium ion adduct of an ethylated cellulose oligomer having a degree of polymerization of about 6 to 9 mers. Thus, the results revealed that cellooligosaccharides having a predetermined degree-of-polymerization distribution were enzymatically synthesized. When 20% DMSO was used as a reaction solvent, the average degree of polymerization (DP) was lower, and the degree-of-polymerization distribution was narrower, than those of the control (–), which was enzymatically synthesized in an HEPES buffer; and the formation of oligomers having a degree of polymerization (n) as high as 9 to 11 was suppressed.

Table 3 shows the results of calculations of the percentage of each degree of polymerization from the MS spectrum data of FIG. 7. As is clear from Table 3, when the mixed solvent was used, the formation of oligomers having a high degree of polymerization was suppressed as compared with the control (–). In Table 3, "0%" means below the detection limit.

TABLE 3

| Reaction solvent | Percentage of each degree of polymerization (%) | | | | | | | | Standard deviation |
|---|---|---|---|---|---|---|---|---|---|
| | 5 | 6 | 7 | 8 | 9 | 10 | 11 | DP | |
| 20% DMSO | 1 | 23 | 43 | 26 | 7 | 1 | 0 | 7.2 | 0.92 |
| (—) | 0 | 6 | 26 | 31 | 26 | 8 | 2 | 8.1 | 1.14 |

Figure 8:
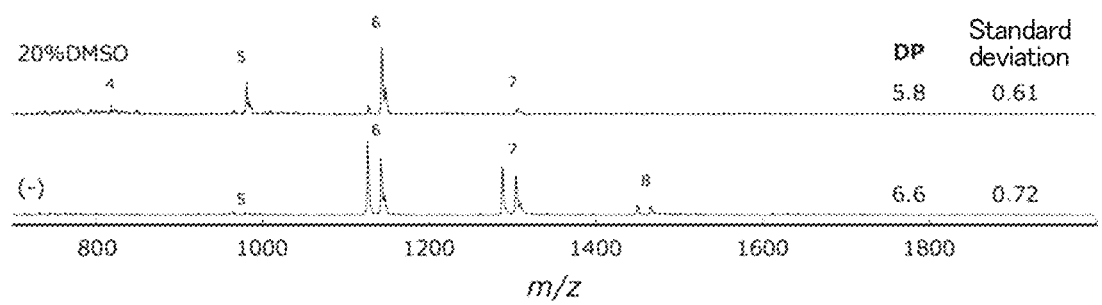
FIG. 8 shows MS spectra of precipitated products in a test of addition of an organic solvent to an octyl glucoside primer synthesis system.

2-2-6. Effect of Addition of Organic Solvent to Octyl Glucoside Primer Synthesis System A precipitated product enzymatically synthesized using an octyl glucoside primer and 20% DMSO as a reaction solvent was purified by repeating the operation of centrifugation and redispersion five times using, as a washing solvent, water containing DMSO in the same proportion as that of the reaction solvent. Thereafter, the resulting precipitated product was subjected to MALDI-TOF-MS spectrum measurement. FIG. 8 shows the obtained MS spectrum, which show multiple peaks whose m/z spacing corresponds to that of a glucosyl unit. Further, each of the detected peaks corresponds to a sodium ion adduct or potassium ion adduct of an octylated cellulose oligomer having a degree of polymerization of about 5 to 7 mers. Thus, the results revealed that cellooligosaccharides having a predetermined degree-of-polymerization distribution were enzymatically synthesized. When 20% DMSO were used as a reaction solvent, the average degree of polymerization (DP) was lower, and the degree-of-polymerization distribution was narrower, than those of the control (–), which was enzymatically synthesized in an HEPES buffer; and the formation of oligomers having a degree of polymerization (n) as high as 7 to 9 was suppressed.

Table 4 shows the results of calculations of the percentage of each degree of polymerization from the MS spectrum data of FIG. 8. As is clear from Table 4, when the mixed solvent was used, the formation of oligomers having a high degree of polymerization was suppressed as compared with the control (–). In Table 4, "0%" means below the detection limit.

TABLE 4

| Reaction solvent | Percentage of each degree of polymerization (%) | | | | | | | Standard deviation |
|---|---|---|---|---|---|---|---|---|
| | 4 | 5 | 6 | 7 | 8 | 9 | DP | |
| 20% DMSO | 1 | 31 | 62 | 7 | 0 | 0 | 5.8 | 0.61 |
| (—) | 0 | 1 | 53 | 36 | 9 | 1 | 6.6 | 0.72 |

While some embodiments of the present invention have been described, these embodiments are presented as examples, and are not intended to limit the scope of the invention. These embodiments can be practiced in various other modes, and various omissions, substitutions, and modifications can be made without departing from the spirit of the present invention. These embodiments, and omissions, substitutions, and modifications thereof are encompassed in the scope and spirit of the invention; and also fall within the scope of the invention described in the claims, and the equivalents thereof.

The invention claimed is:

1. A method for producing a cellooligosaccharide, comprising:
    reacting α-glucose-1-phosphate and at least one primer selected from the group consisting of glucose and alkylated glucose with cellodextrin phosphorylase in a mixed solvent containing water and a water-soluble organic solvent, so as to obtain a cellooligosaccharide having the following structure:

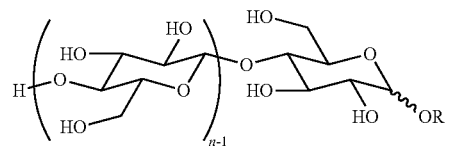

wherein n is a degree of polymerization and an integer of 5 to 11, and R represents a hydrogen or an alkyl group having 1 to 12 carbon atoms, and
an average degree of polymerization is 6.0 to 9.0, and
wherein the amount of the water-soluble organic solvent is 5 to 30 volume % based on the mixed solvent taken as 100 volume %.

2. The method for producing a cellooligosaccharide according to claim 1, wherein the water-soluble organic solvent is at least one member selected from the group consisting of methanol, ethanol, N,N-dimethylformamide, and dimethyl sulfoxide.

3. The method for producing a cellooligosaccharide according to claim 1, wherein the amount of the water-soluble organic solvent is 5 to 20 volume % based on the mixed solvent taken as 100 volume %.

4. The method for producing a cellooligosaccharide according to claim 1, wherein the amount of the water-soluble organic solvent is 10 to 20 volume % based on the mixed solvent taken as 100 volume %.

5. The method for producing a cellooligosaccharide according to claim 1, wherein the average degree of polymerization is 7.2 to 9.0.

6. The method for producing a cellooligosaccharide according to claim 1, wherein the at least one primer is selected from the group consisting of the glucose and an ethyl alkylated glucose as the alkylated glucose, the water-soluble organic solvent is the dimethyl sulfoxide, the amount of the dimethyl sulfoxide is 10 to 25 volume % based on the mixed solvent taken as 100 volume %, the average degree of polymerization is 7.2 to 8.3, and a standard deviation of the degree of polymerization is 0.92 to 1.08.

* * * * *